United States Patent
Avramoff et al.

(10) Patent No.: US 8,865,198 B2
(45) Date of Patent: Oct. 21, 2014

(54) METHOD FOR TREATING A PERIODONTAL DISEASE

(75) Inventors: Avi Avramoff, Haifa (IL); Eyal Shoshani, Jerusalem (IL); Adel Penhasi, Holon (IL); Dan Oren, Kfar Shmariahu (IL)

(73) Assignee: Dexcel Pharma Technologies Ltd., OR Akiva (IL)

( * ) Notice: Subject to any disclaimer, the term of this patent is extended or adjusted under 35 U.S.C. 154(b) by 0 days.

(21) Appl. No.: 13/277,784

(22) Filed: Oct. 20, 2011

(65) Prior Publication Data

US 2012/0100199 A1  Apr. 26, 2012

Related U.S. Application Data

(60) Provisional application No. 61/406,288, filed on Oct. 25, 2010.

(51) Int. Cl.
| | |
|---|---|
| A61F 13/00 | (2006.01) |
| A61K 47/10 | (2006.01) |
| A61K 9/00 | (2006.01) |
| A61K 47/42 | (2006.01) |
| A61K 9/70 | (2006.01) |
| A61K 31/192 | (2006.01) |

(52) U.S. Cl.
CPC .............. *A61K 9/0063* (2013.01); *A61K 47/10* (2013.01); *A61K 47/42* (2013.01); *A61K 9/7007* (2013.01); *A61K 31/192* (2013.01)
USPC ...................................................... 424/422

(58) Field of Classification Search
None
See application file for complete search history.

(56) References Cited

U.S. PATENT DOCUMENTS

| | | |
|---|---|---|
| 4,568,535 A | 2/1986 | Loesche |
| 4,569,837 A | 2/1986 | Suzuki et al. |
| 4,685,883 A | 8/1987 | Jernberg |
| 4,764,377 A | 8/1988 | Goodson |
| 4,892,736 A | 1/1990 | Goodson |
| 5,002,769 A | 3/1991 | Friedman |

(Continued)

FOREIGN PATENT DOCUMENTS

| | | |
|---|---|---|
| EP | 0137668 A2 | 4/1985 |
| EP | 0374531 A2 | 6/1990 |

(Continued)

OTHER PUBLICATIONS

Lindhe et al. Healing following surgical/non-surgical treatment of periodontal disease : A Clinical Study, Journal of Clinical Periodontology, 1982, vol. 9, pp. 115-128.*

(Continued)

*Primary Examiner* — Carlos Azpuru
*Assistant Examiner* — Casey Hagopian
(74) *Attorney, Agent, or Firm* — Pabst Patent Group LLP

(57) ABSTRACT

Provided is a method for treating a periodontal disease affecting a periodontal pocket of a patient. The method includes inserting an oral delivery device into the periodontal pocket at a frequency of about once every 4 days to about once every 6 weeks. The oral delivery device is a controlled release solid unit dosage form suitable for insertion into a periodontal pocket of a patient, including a therapeutically effective amount of at least one anti-inflammatory agent, at least one antibacterial agent, or the combination of at least one anti-inflammatory agent and at least one antibacterial agent.

34 Claims, 1 Drawing Sheet

(56) References Cited

U.S. PATENT DOCUMENTS

| | | | |
|---|---|---|---|
| 5,023,082 | A | 6/1991 | Friedman et al. |
| 5,143,934 | A | 9/1992 | Lading et al. |
| 5,160,737 | A | 11/1992 | Friedman et al. |
| 5,190,981 | A | 3/1993 | Wechter |
| 5,236,355 | A | 8/1993 | Brizzolara et al. |
| 5,308,839 | A | 5/1994 | Golub et al. |
| 5,324,520 | A | 6/1994 | Dunn et al. |
| 5,366,733 | A | 11/1994 | Brizzolara et al. |
| 5,447,725 | A | 9/1995 | Damani et al. |
| 5,702,716 | A | 12/1997 | Dunn et al. |
| 5,902,110 | A | 5/1999 | Alfano et al. |
| 5,972,366 | A | 10/1999 | Haynes et al. |
| 5,980,925 | A | 11/1999 | Jampani et al. |
| 6,159,498 | A | 12/2000 | Tapolsky et al. |
| 6,197,331 | B1 | 3/2001 | Lerner et al. |
| 6,248,363 | B1 | 6/2001 | Patel et al. |
| 6,451,339 | B2 | 9/2002 | Patel et al. |
| 6,685,928 | B2 | 2/2004 | Uhrich et al. |
| 2001/0049363 | A1 | 12/2001 | Rubin et al. |
| 2004/0185009 | A1* | 9/2004 | Penhasi et al. .............. 424/49 |

FOREIGN PATENT DOCUMENTS

| | | |
|---|---|---|
| EP | 0374532 A2 | 6/1990 |
| EP | 0388220 A2 | 9/1990 |
| EP | 1033127 A1 | 9/2000 |
| WO | 88/03021 A2 | 5/1988 |
| WO | 92/00104 A1 | 1/1992 |
| WO | 92/00718 A1 | 1/1992 |
| WO | 95/04520 A1 | 2/1995 |
| WO | 99/04764 A1 | 2/1999 |
| WO | 02/02128 A1 | 1/2002 |
| WO | 2004/084873 A1 | 10/2004 |

OTHER PUBLICATIONS

Renvert et al. "Mechanical and Repeated Antimicrobial Therapy Using a Local Drug Delivery System in the Treatment of Peri-Implantitis: A Randomized Clinical Trial" Journal of Clinical Periodontology 2008;79:836-844.*

Meffert "Periodontitis vs. Peri-implantitis: The Same Disease? The Same Treatment?" Crit Rev Oral Biol Med 1996;7:278-291.*

Axelsson et al J Clin Periodonol. 1978 vol. 5 pp. 133-151: Effect of controlled oral Hygiene procedures on caries and periodontal disease in adults.

Azmak et al J Periodontol. 2002 vol. 73 No. 6 pp. 608-615: The Effect of Subgingival Controlled-Release Delivery of Chlorhexidine Chip onClinical Parameters and Matrix Metalloproteinase-8 Levels in Gingival Crevicular Fluid.

Bär Dentistry | practice | user report; Parodontology, 2008 ZWP 7+8: Successful treatment using laser and chlorhexidine (published in German).

Behjat et al J Intl Food Res. 2009 vol. 16 pp. 243-247: Effect of PEG on the biodegradability studies of Kenaf cellulose—polyethylene composites.

Bernimoulin et al J Clin Periodontol. 1999 vol. 26 pp. 710-715: Repeated local metronidazole-therapy as adjunct to scaling and root planing in maintenance patients.

Chung et al J Periodontol Res. 1997 vol. 32 pp. 172-175.

Editorial team Dexcel® Pharma GmbH—Dentistry/Implantology, Dentalbarometer. Mar. 2007 The struggle against the loss of dental implants (published in German).

Genco J Periodontol. 1981 vol. 52 pp. 545-558: Antibiotics in the Treatment of Human Periodontal Deseases.

Gingivitis—Dental Hygiene and Oral Health—Dec. 19, 2002—Online publication http://www.nau.edu/fronske/dental_hygiene.htm.

Goodson et al J Clin Periodonol. 1979 vol. 6 No. 2 pp. 83-92 Periodontal therapy by local delivery of tetracycline.

Goodson et al J Periodontol. Supp 1985 Special Issue pp. 81-87: Clinical Responses Following Periodontal Treatment byLocal Drug Delivery.

Goodson In: Medical Applications of Controlled Release, vol. II, Applications Evaluation (Langer, R.S., et al., Eds.), CRC Press, Inc., Boca Raton, FL 1984 pp. 115-138.

Heasman et al J Clin Periodontol 1993 vol. 20 pp. 457-464.

Heasman et al J Clin Periodontol 2001 vol. 28 pp. 90-95: Local delivery of chlorhexidine gluconate (PerioChip) in Periodontal maintenance patients.

Jeffcoat et al J Periodontol Res. 1986 vol. 21 pp. 624-633: Flurbiprofen treatment of periodontal disease in beagles.

Jeffcoat et al J Periodontol Res. 1988 vol. 23 pp. 381-385: Flurbiprofen treatment of human periodontitis: effect on alveolar bone height and metabolism.

Jeffcoat et al J Periodontol. 1998 vol. 69 No. 9 pp. 989-997: Adjunctive Use of a Subgingival Controlled-Release Chlorhexidine Chip Reduces Probing Depth and Improves Attachment Level Compared With Scaling and Root Planing Alone.

Jeffcoat et al J Periodontol. 2000 vol. 71 No. 2 pp. 256-262: Use of a biodegradable chlorhexidine chip in the treatment of adult periodontitis: clinical and radiographic findings.

Larsen et al J Clin Periodonto1.1997 vol. 24 pp. 254-259: Development of resistance to metronidazole and minocycline in vitro.

Lenz—Dental Forum—Case study—ZMK, vol. 26, Issue 3, Mar. 2010—Treating parodontitis with an abutment tooth stabilized with a PerioChip.

Lin et al Pharm Res. 1991 vol. 8 No. 9 pp. 1137-1143: The Effect of Plasticizers on Compability, Mechanical Properties, and Adhesion Strength of Drug-Free Eudragit E Films.

Loe et al J Periodontol Res. 1970 vol. 5 pp. 79-83: The effect of mouthrinses and topical application of chlorhexidine on the development of dental plaque and gingivitis in man.

Loe et al J Periodontol. 1965 vol. 36 pp. 5-15: Experimental Gingivitis in Man.

Offenbacher et al J Periodont Res. 1987 vol. 22 pp. 473-481.

Periodontal (gum) disease—Sep. 12, 2002—Online publication http://www.austindental.com/more/gum.shtml.

Periostat® (doxycycline hyclate) 20 mg—Dec. 19, 2002—Online publication http://www.collagenex.com/pr periostat.asp.

Reddy et al J Periodontol. 2003 vol. 74 No. 4 pp. 411-419: Efficacy of controlled-release subgingival chlorhexidine to enhance periodontal regeneration.

Rodrigues et al J Periodontol. 2007 vol. 20 pp. 624-628. Clinical Evaluation of the Use of Locally Delivered Chlorhexidine in Periodontal Maintenance Therapy.

Sela et al J Clin Periodontol. 1986 vol. 13 pp. 783-788: Clinical and microbiological effects of sustained release chlorhexidine in periodontal pockets.

Sellmann J Dentalhygiene User report—Jan. 2008: Protecting the implant (Published in German).

Slots Scan J Dent Res. 1977 vol. 85 pp. 247-254: Microflora in the Healthy Gingival Sulcus in Man.

Socransky J Periodontol. 1977 vol. 48 pp. 497-504: Microbiology of Periodontal disease—Present Status and Future Considarations.

Soskolne et al J Periodontol. 1997 vol. 68 No. 1 pp. 32-38: Sustained local delivery of chlorhexidine in the treatment of periodontitis: a multi-center study.

Soskolne et al J Periodontol. 2003 vol. 74 No. 4 pp. 420-427: Probing Depth Changes Following 2 Years of Periodontal Maintenance Therapy Including Adjunctive Controlled Release of Chlorhexidine.

Stabholz et al Compendium 2000 vol. 21 No. 4 pp. 325-338: Using the PerioChip â in treating adult periodontitis: an interim report.

Vyas, et al J Clin. Pharm. & Therapeutics 2000 vol. 25 pp. 21-42.

Williams et al J Dent Res.1991 vol. 70 #1617 (Abstr) p. 468: Three-year trial of flurbiprofen treatment in humans: post-treatment period.

Williams et al J Periodontol Res. 1984 vol. 19 pp. 633-637.

Williams et al J Periodontol Res. 1987 vol. 22 pp. 403-407.

Williams et al J Periodontol Res. 1988 vol. 23 pp. 166-169: Topical flurbiprofen treatment of periodontitis in beagles.

Albandar JM. Adjunctive antibiotics with nonsurgical periodontal therapy improve the clinical outcome of chronic periodontitis in current smokers. J Evid Based Dent Pract 2012;12 (3 Suppl):63-66.

(56) References Cited

OTHER PUBLICATIONS

Bächter, A., Meyer, U., Kruse-Lösler, B., Joos, U. & Kleinheinz, J. Sustained release of doxycycline for the treatment of peri-implantitis: randomized controlled trial. Br J Oral Maxillofac Surg 2004; 42; 439-444.
Carranza's clinical periodontology. 10th edition. Newman MG, Takei H, Klokkevold PR, Carranza FA eds. Chapter 52: Jolkovsky DL & Ciancio S. Chemotherapeutic agents. pp. 798-812. Jun. 30, 2006.
Clinical periodontology and implant dentistry. 5th edition. Lindhe J, Lang NP, Karring T. eds. Chapter 42: Andrea Mombelli. Antibiotics in periodontal therapy. pp. 882-899. Apr. 15, 2009.
Cortelli JR, Querido SM, Aquino DR, Ricardo LH, Pallos DFBP. Longitudinal clinical evaluation of adjunct minocycline in the treatment of chronic periodontitis. J Periodontol 2006; 77:161-166.
Garrett S, Johnson L, Drisko CH, Adams DF, Bandt C, Beiswanger B, Bogle G, et al. Two multi-center studies evaluating locally delivered doxycycline hyclate, placebo control, oral hygiene, and scaling and root planing in the treatment of periodontitis. J Periodontol 1999; 70:490-503.
Gonzales JR, Harnack L, Schmitt-Corsitto G, Boedeker RH, Chakraborty T, Domann E, Meyle J. A novel approach to the use of subgingival controlled-release chlorhexidine delivery in chronic periodontitis: a randomized clinical trial. J Periodontol 2011; 82:1131-1139.
Greenstein G. Local drug delivery in the treatment of periodontal diseases: assessing the clinical significance of the results. J Periodontol 2006; 77:565-578.
Krayer JW, Leite RS, Kirkwood KL. Non-surgical chemotherapeutic treatment strategies for the management of periodontal diseases. Dent Clin North Am 2010; 54:13-33.
Machion L, Andia DC, Lecio G, Nociti FH Jr, Casati MZ, Sallum AW, Sallum EA. Locally delivered doxycycline as an adjunctive therapy to scaling and root planing in the treatment of smokers: A 2-year follow-up. J Periodontol. 2006; 77:606-613.
Machtei EE, Frankenthal S, Levi G, Elimelech R, Shoshani E, Rosenfeld O, Tagger-Green N, Shlomi B. Treatment of peri-implantitis using multiple applications of chlorhexidine chips: a double-blind, randomized multi-center clinical trial. J Clin Periodontol 2012; 39:1198-1205.
Machtei EE, Hirsh I, Falah M, Shoshani E, Avramoff A, Penhasi A. Multiple applications of flurbiprofen and chlorhexidine chips in patients with chronic periodontitis: a randomized, double blind, parallel, 2-arms clinical trial. J Clin Periodontol 2011; 38:1037-1043.
Matesanz-Perez P, Garcia-Gargallo M, Figuero E, Bascones-Martinez A, Sanz M, Herrera D. A systematic review on the effects of local antimicrobials as adjuncts to subgingival debridement, compared with subgingival debridement alone, in the treatment of chronic periodontitis. J Clin periodontal 2013; 40:227-241.
McColl E, Patel K, Dahlen G, Tonetti M, Graziani F, Suvan J, Laurell L. Supportive periodontal therapy using mechanical instrumentation or 2% minocycline gel: a 12 month randomized, controlled, single masked pilot study. J Clin Periodontol 2006; 33:141-150.
Noyan U, Yilmaz S, Kuru B, Kadir T, Acar O, Büget E. A clinical and microbiological evaluation of systemic and local metronidazole delivery in adult periodontitis patients. J Clin Periodontol 1997; 24:158-165.
Paolantonio M, D'Angelo M, Grassi RF, et al. Clinical and microbiologic effects of subgingival controlled-release delivery of chlorhexidine chip in the treatment of periodontitis: a multicenter study. J Periodontol 2008; 79:271-282.
Rao SK, Setty S, Acharya AB, Thakur SL. Efficacy of locally-delivered doxycycline microspheres in chronic localized periodontitis and on Porphyromonas gingivalis. J Investig Clin Dent 2012; 3:128-134.
Renvert S, Lessem J, Dahlén G, Lindahl C, Svensson M. Topical minocycline microspheres versus topical chlorhexidine gel as an adjunct to mechanical debridement of incipient peri-implant infections: a randomized clinical trial. J Clin Periodontol 2006; 33:362-369.
Renvert S., Lessem J., Dahlén G., Renvert H. & Lindahl C. Mechanical and repeated antimicrobial therapy using a local drug delivery system in the treatment of peri-implantitis: a randomized clinical trial. J Clin Periodontol 2008; 79:836-844.
Sahm, N., Becker, J., Santel, T. & Schwarz, F. Non-surgical treatment of peri-implantitis using an air-abrasive device or mechanical debridement and local application of chlorhexidine: a prospective, randomized, controlled clinical study. J Clinical Periodontol 2011; 38: 872-878.
Salvi GE, Mombelli A, Mayfield L, Rutar A, Suvan J, Garrett S, Lang NP. Local antimicrobial therapy after initial periodontal treatment. J Clin Periodontol 2002; 29: 540-550.
Salvi GE, Persson GR, Heitz-Mayfield LJ, Frei M. & Lang NP. Adjunctive local antibiotic therapy in the treatment of peri-implantitis II: clinical and radiographic outcomes. Clinical Oral Implants Research 2007; 18:281-285.
Van Steenberghe et al, J Periodontol, Jun. 1999, vol. 70, No. 6, pp. 657-667.

\* cited by examiner

METHOD FOR TREATING A PERIODONTAL DISEASE

This is a Non-Provisional Application filed as an application claiming the benefit under 35 U.S.C. §119(e) of U.S. Provisional Application No. 61/406,288, filed on Oct. 25, 2010, the content of which is hereby incorporated by reference in its entirety.

FIELD OF THE INVENTION

This invention relates to an improved method for treating a periodontal disease.

BACKGROUND OF THE INVENTION

Local delivery systems (LDS) of antibacterial agents have shown beneficial effect on pocket reduction and inflammation in chronic periodontitis patients. An example of such a system is the Periochip®. PerioChip® (chlorhexidine gluconate) is a small, rectangular chip for insertion into periodontal pockets. Each PerioChip contains 2.5 mg of chlorhexidine gluconate in a biodegradable matrix of hydrolyzed gelatin (cross-linked with glutaraldehyde). PerioChip also contains glycerin and purified water. Treatment is recommended to be administered once every three months in pockets with a remaining pocket depth of ≥5 mm.

Absorbable periodontal implants have been described which used a hydroxypropylcellulose polymer. Suzuki, Y., et. al., (U.S. Pat. No. 4,569,837) discloses the use of water-soluble polymeric substances (such as methyl cellulose, gelatin, etc.) as a polymeric matrix for a periodontal implant. Lading, P. (U.S. Pat. No. 5,143,934) describes the incorporation of metronidazole into a gel that semi-solidifies in the periodontal pocket as a liquid crystalline formulation. The antibiotic drug is released over about one day as the gel dissolves in the gingival crevicular fluid.

A biodegradable sustained-release composition has been described by Freidman, M. et al., (U.S. Pat. No. 5,023,769) which is capable of delivering a pharmacological composition for a period of time sufficient to treat a periodontal infection. The pharmacological agent (chlorhexidine antiseptic) comprises a polymeric matrix containing a plasticizing agent, and the active agent, wherein the polymeric matrix comprises a cross-linked, water-insoluble protein formed from a water soluble protein.

The compositions described above have varying efficacy in reducing the bacterial load of the periodontal pocket and in reducing pocket depth and gingival level of attachment. None of the above mentioned formulations are particularly efficacious in causing alveolar bone regrowth or even in arresting alveolar bone resorption.

One of the drugs that is known in its ability to reduce alveolar bone resorption is flurbiprofen (FBP). FBP is a non-steroidal anti-inflammatory drug (NSAID) which also exhibits analgesic and anti-pyretic activity. FBP inhibits prostaglandin synthesis by inhibition of cyclooxygenase, an enzyme that catalyses the formation of prostaglandin precursors from arachidonic acid. Wechter, W. J. (European patent No. 137, 668 B1) suggests the use of FBP for the treatment of bone resorption and the inducing of bone growth.

Williams et al (J. Perio. Res. 19:633-637, 1984; 22:403-407, 1987; 23:166-169, 1988) and Jeffcoat et al (J. Perio. Res. 21:624-633, 1986) demonstrated that devices and topical application of FBP to beagle dogs for 6-12 months inhibited alveolar bone loss in naturally occurring periodontitis. Offenbacher et al (J. Perio. Res. 22:473-481, 1987) demonstrated that FBP administered deviceatically to Macaca mulatta monkeys with experimentally induced periodontal disease resulted in significant inhibition of attachment, bleeding on probing and gingival redness. Chung et al (J. Perio. Res. 32:172-175, 1997) tested drug (FBP and others)-loaded biodegradable membrane for guided bone regeneration (GBR). The loaded membrane was effective for osteoid tissue and new bone formation in the bony defect prepared in rat calvaria to compare with that by unloaded membrane. The successful results seen in animal models treated with FBF led to the conclusion that clinical studies could be performed in patients with moderate to severe periodontal disease.

Jeffcoat et al (J. Perio. Res. 23:381-385, 1988) were the first investigators who demonstrated the clinical effects of FBP on the progression of periodontal disease. As evidenced by standardized radiography and reduced radiopharmaceutical uptake, treatment with FBP (100 mg/day) for two months increased bone metabolism. A study for 24 months using FBP by Williams et al (J. Dental Res. 70:468, 1991) found that the FBP—oral administration treated patient group showed reduction in bone loss. This demonstrated that FBP treatment can be a significant inhibitor of alveolar bone loss. Heasman et al (J. Clin. Periodontol, 20:457-464, 1993) examined the effect of FBP given topically (toothpaste, 1% w/w) twice daily for 12 months to patients with periodontal disease. The FBP treated group showed statistically significant bone gain. This suggests that the topical application of FBP may have a positive bone gain effect in humans.

Dimani, N. C. (U.S. Pat. No. 5,447,725) suggests a delivery device that hardens on contact with the periodontal tissue after a solvent is leached out and that releases FBP or other drugs in the periodontal pocket. The material is inserted into the periodontal pocket as a gel from a syringe and hardens in situ. Stringing an exact dose of a gel into a body crevice such as a periodontal pocket and having a known dose of the drug solidifying therein is difficult to carry out and difficult to control.

Friedman et al (U.S. Pat. No. 5,023,082) discloses biodegradable sustained-release liquid compositions capable of achieving the sustained release of a pharmaceutical agent such as an anti-inflammatory agent. The liquid precursor compositions can be formed into solid implant devices after administration which may be used to treat diseases such as periodontal disease which require prolonged drug release.

Friedman et al (U.S. Pat. No. 5,160,737) discloses a liquid methacrylic acid copolymer composition that contains a release adjusting agent and a pharmacological agent. The composition forms a solid film upon drying, and is capable of accomplishing the sustained release of the pharmacological agent such as to permit its use in the treatment or prevention of dental or dermatological conditions.

Lerner et al (U.S. Pat. No. 6,197,331) discloses a controlled-release solid composition for the oral cavity or "pharmaceutical oral patch" that adheres to hard dental surfaces, such as teeth and dentures, and releases an active pharmaceutical agent into the oral cavity. Release of the agent is for a predetermined period of time and at a predetermined sustained concentration. The site of action of the agent is local or device.

Uhrich et al (U.S. Pat. No. 6,685,928) discloses methods of promoting healing through enhanced regeneration of tissue (e.g. hard tissue or soft tissue) by contacting the tissue or the surrounding tissue with an anti-inflammatory agent in a carrier comprising aromatic polyanhydrides. These methods are useful in a variety of dental and orthopedic applications.

WO 2004/084873 discloses an oral delivery system for the treatment of periodontal disease, being in a solid unit dosage form for administration to a patient and comprising: (i) a biodegradable or bioerodible pharmaceutically acceptable polymer; (ii) a therapeutically effective amount of at least one antibacterial agent; and (iii) a therapeutically effective amount of at least one anti-inflammatory agent, the relative weight ratio between the antibacterial agent and the anti-inflammatory agent ranking from about 7:1 to about 1:5. The system may further comprise at least one of a cross-linking agent, a plasticizing agent, a wetting agent, a suspending agent, a surfactant and a dispersing agent.

SUMMARY OF THE INVENTION

It has now been surprisingly discovered that the oral delivery device as disclosed in the prior art may be administered at a significantly higher frequency than was previously known, with improved therapeutic results.

Thus, the present invention provides a method for treating a periodontal disease affecting a periodontal pocket of a patient in need comprising inserting an oral delivery device into the periodontal pocket at a frequency of about once every 4 days to about once every 6 weeks, wherein the oral delivery device is a controlled release solid unit dosage form suitable for insertion into a periodontal pocket of a patient, comprising a therapeutically effective amount of an active ingredient selected from:

i) at least one anti-inflammatory agent,
  ii) at least one antibacterial agent, and
  iii) the combination of at least one anti-inflammatory agent and at least one antibacterial agent.

In one embodiment, the oral delivery device further comprises a biodegradable pharmaceutically acceptable water-insoluble polymer in the form of a matrix, wherein the active ingredient is dispersed or dissolved within the matrix.

In another embodiment, the biodegradable pharmaceutically acceptable water-insoluble polymer is degradable by enzymatic degradation, physical disintegration or a combination thereof.

In one embodiment, the water-insoluble polymer comprises a water-soluble polymer rendered water-insoluble by the addition of a cross-linking agent in an amount sufficient to render said polymer water-insoluble, while permitting the release of said anti-inflammatory agent or said antibacterial agent from said delivery device.

In a further embodiment, the oral delivery device optionally comprises a plasticizing agent.

In another embodiment, the oral delivery device optionally comprises at least one of a surfactant, a wetting agent, a suspending agent and a dispersing agent.

In a further embodiment, the oral delivery device optionally comprises an enzymatically biodegradable pharmaceutically acceptable water soluble polymer dispersed or dissolved within the matrix.

In one embodiment, the oral delivery device is inserted at a frequency of once every 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or 46 days.

In a further embodiment, the oral delivery device is inserted at a frequency of every 7-14 days.

In a still further embodiment, the oral delivery device is inserted at a frequency of once every two weeks for a period of the earlier of three months or until healing, with healing being defined as a Periodontal Pocket Depth (PPD) of less than 5 mm.

In another embodiment, the frequency of insertion is decreased as the PPD decreases.

In this specification, the following terms have the following meanings:

"solid unit dosage form" means not a liquid, and includes semi-solid, paste, ointment and gel.

"controlled release" means not an immediate release of all of the active ingredient, and includes sustained release, delayed release and extended release.

In another aspect of the invention, there is provided a use of an oral delivery device as defined in the specification in the preparation of a device adapted for insertion into the periodontal pocket for the treatment of periodontal disease according to the method of the invention.

In one embodiment of the invention, the physical disintegration is by hydration and swelling of the water-insoluble polymer. In another embodiment, the biodegradable water-insoluble polymer is not degradable by hydrolysis. In a further embodiment, the water-insoluble polymer is present at a concentration of from about 20% to about 70%.

One embodiment of the delivery device that would be most advantageous would be one that has an exact dose of drug predetermined, is easy to insert, is retained in a periodontal pocket without the need of adhesives to keep it from falling out, gives sustained release of the anti-inflammatory drug over several days, and biodegrades so that there is no need for the removal of the device after the treatment period. Ease of insertion and dose control can be obtained by having the delivery device preformed into a rigid thin film that easily slips into a crevice such as a periodontal pocket with the aid of a simple tweezers. The adherence of the dosage form to the inside of the pocket is obtained by the drug delivery device softening and swelling, thereby adhering to the inside of the pocket.

The precursor solutions to drug delivery devices of this invention are used to form drug delivery devices that are polymeric solids that may be cast as films, pellets, granules, cylinders or any other convenient shape for the task at hand. The devices allow local delivery of the drug at the target site. The devices may be used as implants for the extended delivery of drug. The devices may also be used as inserts to body crevices as well as drug delivery devices in the body in general and, in one embodiment, in the oral cavity. Most preferentially, the devices may be used as an insert into periodontal crevices or pockets, or as an implant in periodontal surgery.

A drug delivery device for implantation in the body or insertion in a crevice in the body will preferentially be one that can target the drug to the organ desired, deliver the drug in a local fashion, and degrade in the body to harmless by-products so that the device need not be removed when it has finished its useful function. Preformed devices would negate the dose control problem. Both the in situ and preformed polymers of this sort tend to biodegrade slowly and are useful for delivery devices designed for prolonged release of the active ingredient in a 1-2 weeks time frame. They do, however, biodegrade to amino acids which are biocompatible and non toxic. Poly amino acids and proteins have been found useful as the basis for drug delivery devices since their degradation products are harmless amino acids and their biodegradation is facile in many parts of the body.

Useful polymers for drug delivery include cross-linked water-soluble protein, cellulose or cellulose derivative, starch or starch derivative, glyceryl monostearate, carbomer, PVP (polyvinylpyrrolidone), gum, acacia gum, guar gum, polyvinyl alcohol, polyhydroxyethyl metacrylate, polyhydroxyethyl metacrylate polyacrylic acid, polyacryl amide and polyethylene glycols, an enzyme and fibrinogen. For example, proteins derived from connective tissue such as collagen and gelatin, and proteins of the albumin class that may be derived from milk, serum, or from vegetable sources may be used, with gelatin and hydrolyzed gelatin being the most preferable. In one embodiment, the hydrolyzed gelatin may have a molecular weight in the range of 1-20 K Dalton. Proteins, however, tend to be water soluble. In a soluble form the protein is less useful for sustained release of a drug since its solubilization will remove it from the body in too short a time. It is therefore desirable to render the protein water insoluble while maintaining its ability to biodegrade through normal enzymatic processes and permitting the release of the anti-inflammatory agent from the delivery device. This insolubilization of the protein may be done by making insoluble salts of the protein, insoluble complexes of the protein or most preferably by crosslinking the protein. In one embodiment, a water-soluble polymer is cross-linked by a curing process in the presence of a cross-linking agent, wherein said curing process is selected from the group consisting of heat, humidity, pressure, radiation, and the vapors of a cross-linking agentSince proteins in general contain lysine and arginine residues with amino reactive groups and serine, threonine and tyrosine with hydroxyl side chains, one preferable and well accepted method of crosslinking proteins is with aldehydes or dialdehydes. Formaldehyde, carbodiimide and more preferably glutaraldehyde are well known in the art as methods of crosslinking proteins. The crosslinked protein is rendered insoluble but its ability to be degraded by proteases in the body is maintained. The amount of crosslinking can be controlled by the ratio of the crosslinking agent to the protein side groups with which it is to react. The more heavily crosslinked the protein the less soluble it will be and the more slowly it will be biodegraded by protease enzymes. For example the most preferable amount of glutaraldehyde for crosslinking hydrolyzed gelatin has been found to be the amount that is stoichiometric with the amino side chains in the protein.

While for certain uses (e.g. the insertion of a depot of drug into the body where a crevice is not available) the insertion of liquid formulations may be easier than a preformed solid dosage form, in general a preformed solid dosage form is easier to handle and insert into an open crevice and gives better control of the drug dose. The incorporation of the drug in the delivery device must be uniform so as to keep tight control over the dosing level. If one chooses crosslinked proteins as the delivery device of choice because of its delivery, degradation, and non toxic by-product properties, one is faced with a problem of incorporating non water soluble drugs into such a device. While many methods exist to form homogeneous mixtures, the drug would not be incorporated into the matrix in a complete fashion. When all the components are dissolved in a solution the mixture of the components upon solidification is considerably more intimate and the control of the drug delivery from the crosslinked protein is much enhanced.

Many drugs that are not soluble to any extent in aqueous solutions are soluble in alcohol solutions. The alcohols useful with the aqueous solutions of the proteins are preferably ethanol, isopropanol and n-propanol, with ethanol being the most preferable. Proteins of low molecular weight and a relatively high proportion of hydrophobic side groups do not precipitate from aqueous solution when a certain proportion of alcohol is added. A preferable protein with regards to this property is hydrolyzed gelatin of number average molecular weight less than 20,000 and most preferably less than 13,000 but more than 1000. This protein is stable in solutions that contain over 50% ethanol allowing the incorporation of aqueous solutions of non water soluble drugs that are soluble in the alcohol.

A solid device for insertion into a body crevice needs to be rigid enough to be inserted against a certain amount of back pressure exhibited by the frictional forces on the device when being inserted, but pliable enough so as not to break and pliable enough to conform to the contour of the crevice. In one embodiment, plasticizers are added to formulations to give the desired flexibility. For crosslinked protein and/or non water soluble polymer formulations, possible plasticizers are glycol derivatives, phthalates, citrate derivatives, benzoates, butyl or glycol esters of fatty acids, refined mineral oils, camphor, oleic acid, castor oil, corn oil and sugar alcohols. The type and the amount of the plasticizer will control the flexibility of the composition. Preferred plasticizers for the device which comprising crosslinked protein are sorbitol and glycerin with glycerin being the most preferred plasticizer. For a device comprising a non water soluble polymer, a preferred plasticizer is triethyl citrate. The preferred amount of plasticizer is between 1, 2, 3, 4, 5, 6 or 7% and 15, 16, 17, 18, 19, 20, 21, 22, 23, 24 or 25% (w/w of the drug delivery composition), and most preferably 6-16%.

A variety of pharmacological agents may be incorporated into the precursor solutions and thus into the drug delivery devices described herein. In one embodiment, more than one pharmacological agent can be incorporated into a drug delivery device whether they be of the same therapeutic category (e.g. two or more anti-inflammatory drugs) or of different therapeutic categories, with the exception of an anti-bacterial agent (e.g. one or more anti-fungal drugs, or one or more anti-inflammatory drug and one or more anti-neoplastic drug). In one embodiment, the anti-inflammatory agent is hydrophobic or non-water soluble. The amount of drug to be incorporated into the drug delivery composition depends on the intended therapeutic use and can be determined by one skilled in the art. The drug can be present in the drug delivery composition from 0.1 to 50% (w/w), most preferably 15-45% (w/w).

Examples of antibacterial agents include sulfonamides, phenolics, quaternary ammonium salts, chlorhexidine (CHX) and salts thereof, antibiotics such as penicillins, cephalosporins, tetracycline, doxycycline, chloramphenicol, and erythromycin. A preferred antibacterial agent is CHX di-gluconate.

A particularly preferred anti-inflammatory pharmacological agent for this delivery device is one capable of healing the periodontal tissue or one that can retard bone resorption or induce bone regrowth. Examples of such drugs are bone growth factors, bisphosphonates and FBP. Delivery devices with these drugs may be inserted surgically in the body in proximity to the site where their effect is required. The drug will be released over a prolonged period of time while the delivery device is biodegraded into harmless products. Alternately, the delivery device can be inserted into body cavities in proximity to the site of action, such as a periodontal pocket. One embodiment of this invention is to the incorporation of FBP into the delivery device and its insertion either into a periodontal pocket for the arresting of alveolar bone resorption and for the initiation of bone regrowth, or its implantation under the gum during periodontal surgery. A further preferred usage of the drug delivery device is as an adjunct treatment to periodontal surgery where it is inserted into the periodontal pockets both before and after the periodontal surgery.

Further embodiments of this invention are to the incorporation of drugs that will treat inflammation in a site in the body where the inflammation needs to be treated. Again, the drug delivery device can be inserted into body crevices that exist or are implanted in a surgical procedure. Examples of drugs whose efficacious amounts for use in the delivery device of the invention may be determined include anti-inflammatory agents including steroidal anti-inflammatory agents such as dexamethasone, budesonide, beclomethasone, and hydrocortisone.

Anti-Inflammatory agents are a well known class of pharmaceutical agents which reduce inflammation by acting on body mechanisms (Stedman's Medical Dictionary 26 ed., Williams and Wilkins, (1995); Physicians Desk Reference 51 ed., Medical Economics, (1997)).

Anti-inflammatory agents useful in the methods of the invention include Non-steroidal Anti-Inflammatory Agents (NSAIDS). NSAIDS typically inhibit the body's ability to synthesize prostaglandins. Prostaglandins are a family of hormone-like chemicals, some of which are made in response to cell injury. Specific NSAIDS approved for administration to humans include naproxen sodium, diclofenac, sulindac, oxaprozin, diflunisal, aspirin, piroxicam, indomethacin, etodolac, ibuprofen, fenoprofen, ketoprofen, mefenamic acid, nabumetone, tolmetin sodium, and ketorolac tromethamine.

Other anti-inflammatory agents useful in the methods of the invention include salicylates, such as, for example, salicylic acid, acetyl salicylic acid, choline salicylate, magnesium salicylate, sodium salicylate, olsalazine, and salsa late.

Other anti-inflammatory agents useful in the methods of the invention include cyclooxygenase (COX) inhibitors. COX catalyzes the conversion of arachidonate to prostaglandin H2 (PGH2); a COX inhibitor inhibits this reaction. COX is also known as prostaglandin H synthase, or PGH synthase. Two Cox genes, Cox-1 and Cox-2 have been isolated in several species. COX-2 is tightly regulated in most tissues and usually only induced in abnormal conditions, such as inflammation, rheumatic and osteo-arthritis, kidney disease and osteoporosis. COX-1 is believed to be constitutively expressed so as to maintain platelet and kidney function and integral homeostasis. Typical COX inhibitors useful in the methods of the invention include etodolac, celebrex, meloxicam, piroxicam, nimesulide, nabumetone, and rofecoxib.

In one embodiment of the invention, anti-inflammatory agents that can be incorporated into a polymer matrix for administration in the methods of the invention include: 3-amino-4-hydroxybutyric acid, aceclofenac, acemetacin, acetaminosalol, alclofenac, alminoprofen, α-bisabolol, paranyline, amfenac, bromfenac, benoxaprofen, benzpiperylon, bermoprofen, bromosaligenin, bucloxic acid, bufexamac, bumadizon, butibufen, carprofen, cinmetacin, clidanac, clopirac, diclofenac, diclofenac sodium, diflunisal, ditazol, enfenamic acid, ε-acetamidocaproic acid bendazac, etodolac, etofenamate, felbinac, fenbufen, fenclozic acid, fendosal, fenoprofen, fentiazac, fepradinol, flufenamic acid, flunoxaprofen, flurbiprofen (FBP), gentisic acid, glucametacin, glycol salicylate, ibufenac, ibuprofen, ibuproxam, indomethacin, indoprofen, isofezolac, isoxepac, isoxicam, ketoprofen, ketorolac, lomoxicam, lonazola, lonazolac, loxoprofen, meclofenamic acid, mefenamic acid, meloxicam, mesalamine, metiazinic acid, mofebutazone, mofezolac, naproxen, niflumic acid, olsalazine, oxaceprol, oxametacine, oxaprozin, oxicams, oxyphenbutazone, paranyline, parsalmide, perisoxal, phenyl salicylate, pirazolac, piroxicam, pirprofen, pranoprofen, proprionic acids, protizinic acid, salacetamide, salicilic acid, salicylamide O acetic acid, salicylsulfuric acid, salsalate, sulfasalazine, sulindac, suprofen, suxibuzone, talniflumate, tenoxicam, terofenamate, tiaprofenic acid, tiaramide, tinoridine, tolfenamic acid, tolmetin, tropesin, xenbucin, ximoprofen, zaltoprofen, zileuton and zomepirac.

For any anti-inflammatory agent referred to herein by a trade name it is to be understood that either the trade name product or the active ingredient possessing anti-inflammatory activity from the product can be used.

In one embodiment, the anti-inflammatory agent and the water-insoluble polymer are present at a relative weight ratio which ranges from about 2:1 to about 1:3. In another embodiment, the plasticizing agent and the polymer are present at a relative weight ratio which ranges from about 1:10 to about 1:2.

A further embodiment of this invention is the incorporation of the NSAID drugs listed above or morphine, codeine, or other anti pain agents for the control of pain from a localized site in the body. Insertion of the drug delivery device will allow efficacious levels of the drug to be delivered over a prolonged period at the site of action.

Further embodiments of this invention are to the incorporation of anti-neoplastic agents including methotrexate, 5-fluorouracil, tamoxifen, chlorambucil, melphalan, mercaptopurine, etoposide, and doxorubicin. Surgical implantation of the device in proximity of the tumor will give high concentration of the chemotherapeutic agent at the tumor site.

When incorporating drugs into the precursor solution it may be advantageous to include surface active agents in order to enhance solubilization of the components and to stabilize the solutions. The surface active agent may be present in amounts that vary from 0 to about 20% of the delivery device. Surfactants that may be of use in formulating the precursor solutions of this invention include polysorbate 80 (Tween 80), anionic emulsifying wax (Crodex A), and sodium lauryl sulfate. In one embodiment of this invention the surface active agents are omitted.

This precursor solution can be formed into various drug delivery devices that are polymeric solids that may be cast as films, pellets, granules, cylinders or any other convenient shape for the task at hand. The most preferable form is when cast as thin films. To form thin films the precursor mixture poured into leveled trays and is dried at room temperature. In one embodiment, the film is from about 3 to about 6 mm in length and from about 1 to about 5 mm in width and from about 0.01 to about 1.0 mm in thickness.

One preferred embodiment of the invention comprises a water soluble protein that is stable in solutions of more than 50% water/alcohol, i.e. hydrolyzed gelatin of number average molecular weight less than 20000 most preferably less than 13,000 but more than 1000. The alcohol used is ethanol and the ethanol to water ratio is between 0.1- to 1.0.

The first preferred composition of the precursor solution is hydrolyzed gelatin 6.8 parts, FBP 2.0 parts, glycerin 1.2 parts, glutaraldehyde solution (25% in water) 2.2 parts, Polysorbate 80 0.2 parts, water 72.0 parts and ethanol 15.6 parts. This formulation when dried to a thin film of 0.35 mm thickness gives a drug delivery device with the following composition:

| | |
|---|---|
| crosslinked hydrolyzed gelatin | 68.4% |
| FBP | 18.9% |
| glycerin | 10.9% |
| polysorbat 80 | 1.8% |

The second preferred composition of the precursor solution is hydrolyzed gelatin 8.1 parts, FBP 3.8 parts, glycerin 1.4 parts, glutaraldehyde solution (25% in water) 1.5 parts, Polysorbate 80 0.3 parts, water 69.0 parts and ethanol 15.9 parts. This formulation when dried to a thin film of 0.35 mm thickness gives a drug delivery device with the following composition:

| | |
|---|---|
| crosslinked hydrolyzed gelatin | 54.2% |

-continued

|              |       |
|--------------|-------|
| FBP          | 31.0% |
| glycerin     | 12.9% |
| polysorbat 80| 1.9%  |

The third preferred composition of the precursor solution is hydrolyzed gelatin 11.0 parts, FBP 4.9 parts, glycerin 2.0 parts, glutaraldehyde solution (25% in water) 3.7 parts, Polysorbate 80 0.2 parts, water 59.3 parts and ethanol 19.0 parts. This formulation when dried to a thin film of 0.35 mm thickness gives a drug delivery device with the following composition:

|                              |       |
|------------------------------|-------|
| crosslinked hydrolyzed gelatin | 62.7% |
| FBP                          | 25.7% |
| glycerin                     | 10.3% |
| polysorbat 80                | 1.3%  |

The thin films of the drug delivery device can be cut into any convenient shape. For use in a periodontal pocket the films can be cut to the dimensions of about 4×5×0.35 mm which is a size appropriate for inserting into a periodontal pocket. The thin film embodiments of this invention can be cut into any convenient shape for implantation or insertion in the body.

Treatment of patients with periodontitis according to the method of the invention is another aspect of the current invention.

Delivery devices containing steroidal or NSAID drugs can be inserted at or in proximity to a site suffering from an inflammatory process. Delivery devices containing FBP or other NSAIDs or other bone growth factors can be inserted at or in proximity to a site that requires bone growth. Delivery devices containing antibiotics, antimicrobials, or anti fungal agents can be inserted at or in proximity to a site where the action of these drugs are called for and delivery devices containing anti-neoplastic agents can be inserted at or in proximity to a tumor site.

The full contents of all publications mentioned in this specification are hereby incorporated by reference.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 shows results using the FBP chip and FIG. 2 shows results using the CHX chip.

DETAILED DESCRIPTION OF EMBODIMENTS

The aim of the present randomized, double-blinded, parallel, 2-arm clinical study was to examine the safety and efficacy of multiple application of a CHX Chip and FBP Chip in subjects with chronic periodontitis. The Chips (=solid oral delivery device) were prepared as disclosed in U.S. Pat. No. 5,023,769 and in WO 2004/084873.

Sixty subjects were accepted and randomized into CHX and FBP groups. Following oral hygiene instruction and full mouth scaling, baseline measurements of PPD and Bleeding On Probing (BOP) were performed.

Example 1

The efficacy of the FBP chip was investigated under 2 different clinical protocols and PPD reduction was measured in mm. In the first clinical study the FBP Chip was inserted into the periodontal pocket every 6 weeks. In the second clinical study the FBP Chip was inserted into the periodontal pocket every week for the first month and every other week for the second month.

Figure 1:
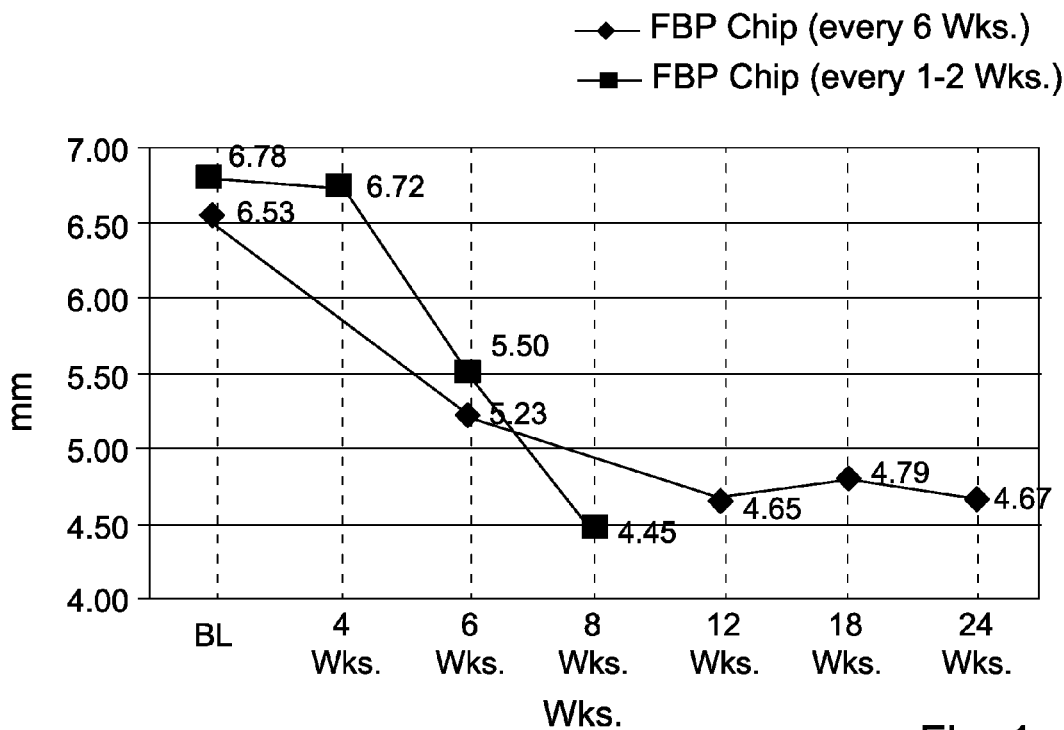
FIGS. 1 & 2 are graphs showing the relationship between PPD in mm as a function of time after insertion of a solid oral delivery device (chip).

The results are presented in FIG. 1. It may be seen that while the every 6 Wks. protocol resulted in a PPD reduction of 1.86 mm after 6 months, the every 1-2 Wks. protocol resulted in a PPD reduction of 2.33 mm after only 2 months. Thus, it may be seen that the increased frequency of insertion gave superior results.

Example 2

The efficacy of the CHX chip was investigated under 3 different clinical protocols and PPD reduction was measured in mm. In the first clinical study CHX was inserted into the periodontal pocket every 3 months. In the second clinical study CHX Chip was inserted into the periodontal pocket every 6 Wks. In the third clinical study CHX Chip was inserted into the periodontal pocket every week for the first month and every other week for the second month.

Figure 2:
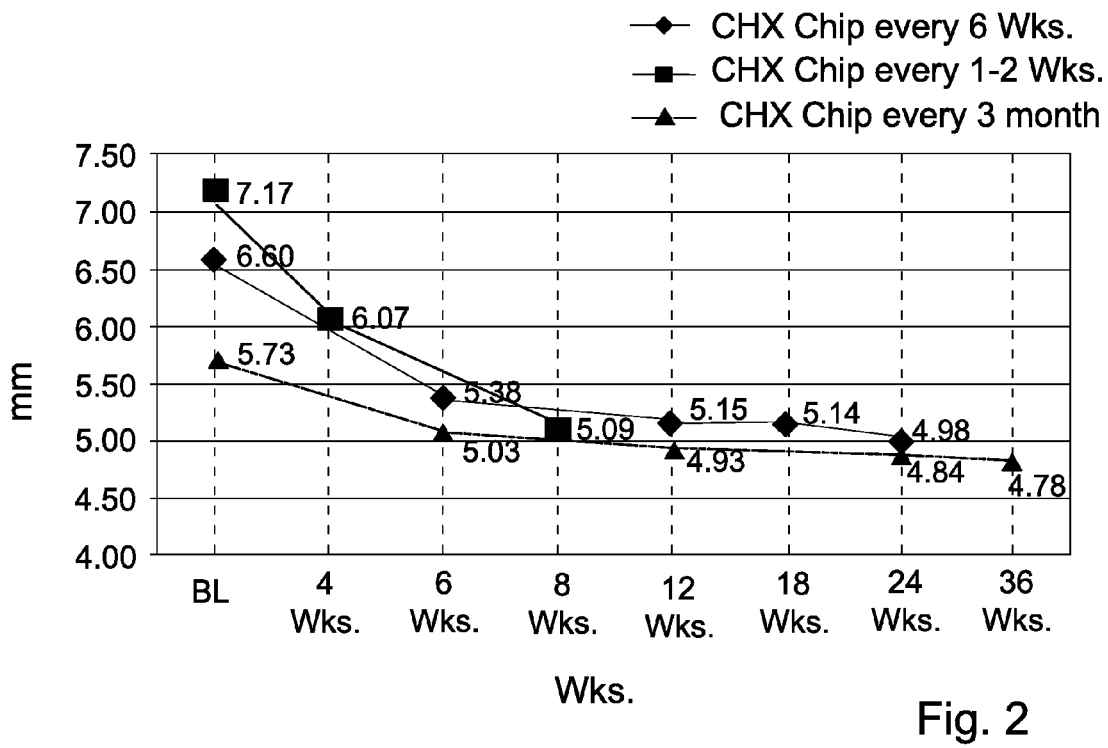

The results are presented in FIG. 2. It may be seen that while the CHX Chip every 3 months protocol resulted in a PPD reduction of 0.95 mm after 9 months, the protocol of every 6 Wks resulted in a PPD reduction of 1.62 mm after 6 months and the protocol of CHX Chip every 1-2 Wks resulted in a further PPD reduction of 2.08 mm after only 2 months.

Conclusion: increased frequency of chip insertion containing either CHX or FBP into periodontal pockets resulted in a significant improvement in the periodontal condition in the periodontal pockets sites in a shorter period of time.

The invention claimed is:

1. A method for treating a periodontal disease affecting a periodontal pocket of a patient in need comprising inserting a solid biodegradable oral delivery device into the periodontal pocket at a frequency of every 7-14 days,
    wherein the solid biodegradable oral delivery device is a controlled release solid unit dosage form suitable for insertion into a periodontal pocket of a patient, comprising a therapeutically effective amount of an active ingredient selected from the group consisting of:
        i) at least one anti-inflammatory agent,
        ii) at least one antibacterial agent, and
        iii) the combination of at least one anti-inflammatory agent and at least one antibacterial agent;
    wherein said solid biodegradable oral delivery device is a chip.

2. The method of claim 1, wherein the oral delivery device further comprises a biodegradable pharmaceutically acceptable water-insoluble polymer in the form of a matrix, wherein the active ingredient is dispersed or dissolved within the matrix.

3. The method of claim 2, wherein the biodegradable pharmaceutically acceptable water-insoluble polymer is degradable by enzymatic degradation, physical disintegration or a combination thereof.

4. The method of claim 2, wherein the biodegradable water-insoluble polymer is not degradable by hydrolysis.

5. The method of claim 2, wherein the water-insoluble polymer comprises a water-soluble polymer rendered water-insoluble by the addition of a cross-linking agent in an amount sufficient to render the polymer water-insoluble, while permitting the release of the anti-inflammatory agent or the antibacterial agent from the delivery device.

6. The method of claim 1, wherein the oral delivery device optionally comprises a plasticizing agent.

7. The method of claim 6, wherein the plasticizing agent is glycerin.

8. The method of claim 1, wherein the oral delivery device optionally comprises at least one of a surfactant, a wetting agent, a suspending agent and a dispersing agent.

9. The method of claim 1, wherein the oral delivery device optionally comprises an enzymatically biodegradable pharmaceutically acceptable water soluble polymer dispersed or dissolved within the matrix.

10. The method of claim 1, wherein the oral delivery device is inserted at a frequency of once every 7, 8, 9, 10, 11, 12, 13, 14 days.

11. The method of claim 1, wherein the oral delivery device is inserted at a frequency of every 14 days for a period of the earlier of three months or until healing of the periodontal pocket.

12. The method of claim 2, wherein the water-insoluble polymer is selected from the group consisting of cross-linked water-soluble protein, cellulose or cellulose derivative, starch or starch derivative, glyceryl monostearate, carbomer, PVP (polyvinylpyrrolidone), gum, acacia gum, guar gum, polyvinyl alcohol, polyhydroxyethyl metacrylate, polyhydroxymethyl metacrylate polyacrylic acid, polyacryl amide and polyethylene glycols.

13. The method of claim 12, wherein the water-soluble protein is selected from the group consisting of gelatin, collagen, albumin, an enzyme and fibrinogen.

14. The method of claim 13, wherein the gelatin is hydrolyzed gelatin.

15. The method of claim 5, wherein the water-soluble polymer is cross-linked by a curing process in the presence of a cross-linking agent, wherein the curing process is selected from the group consisting of heat, humidity, pressure, radiation, and the vapors of a cross-linking agent.

16. The method of claim 5, wherein the water-insoluble polymer is cross-linked in the presence of one or more of glutaraldehyde, formaldehyde, and carbodiimide.

17. The method of claim 2, wherein the water-insoluble polymer is present at a concentration of from about 20% to about 70%.

18. The method of claim 1, wherein the anti-inflammatory agent is a non-steroidal anti-inflammatory agent (NSAID).

19. The method of claim 18, wherein the non-steroidal anti-inflammatory agent is selected from the group consisting of 3-amino-4-hydroxybutyric acid, aceclofenac, acemetacin, acetaminosalol, alclofenac, alminoprofen, α-bisabolol, paranyline, amfenac, bromfenac, benoxaprofen, benzpiperylon, bermoprofen, bromosaligenin, bucloxic acid, bufexamac, bumadizon, butibufen, carprofen, cinmetacin, clidanac, clopirac, diclofenac, diclofenac sodium, diflunisal, ditazol, enfenamic acid, ε-acetamidocaproic acid bendazac, etodolac, etofenamate, felbinac, fenbufen, fenclozic acid, fendosal, fenoprofen, fentiazac, fepradinol, flufenamic acid, flunoxaprofen, flurbiprofen (FBP), gentisic acid, glucametacin, glycol salicylate, ibufenac, ibuprofen, ibuproxam, indomethacin, indoprofen, isofezolac, isoxepac, isoxicam, ketoprofen, ketorolac, lomoxicam, lonazola, lonazolac, loxoprofen, meclofenamic acid, mefenamic acid, meloxicam, mesalamine, metiazinic acid, mofebutazone, mofezolac, naproxen, niflumic acid, olsalazine, oxaceprol, oxametacine, oxaprozin, oxicams, oxyphenbutazone, paranyline, parsalmide, perisoxal, phenyl salicylate, pirazolac, piroxicam, pirprofen, pranoprofen, proprionic acids, protizinic acid, salacetamide, salicilic acid, salicylamide O-acetic acid, salicylsulfuric acid, salsalate, sulfasalazine, sulindac, suprofen, suxibuzone, talniflumate, tenoxicam, terofenamate, tiaprofenic acid, tiaramide, tinoridine, tolfenamic acid, tolmetin, tropesin, xenbucin, ximoprofen, zaltoprofen, zileuton and zomepirac.

20. The method of claim 19, wherein the anti-inflammatory agent is FBP.

21. The method of claim 1, wherein the anti-bacterial agent is selected from the group consisting of sulfonamides, phenolics, quaternary ammonium salts, chlorhexidine and salts thereof, and antibiotics.

22. The method of claim 21, wherein the antibacterial agent is chlorhexidine di-gluconate.

23. The method of claim 1, wherein the device in the form of a film, pellet, granule or cylinder.

24. The method of claim 1, wherein the periodontal disease is periodontitis.

25. The method of claim 1, wherein the treatment is an adjunct treatment to periodontal surgery, where the device is inserted into a periodontal pocket before and/or after the periodontal surgery.

26. The method of claim 21, wherein the antibiotics are selected from the group consisting of penicillins, cephalosporins, tetracycline, doxycycline, chloramphenicol, and erythromycin.

27. The method of claim 1, wherein said solid biodegradable oral delivery device is inserted into the periodontal pocket at least 4 consecutive times.

28. The method of claim 27, wherein said solid biodegradable oral delivery device is inserted into the periodontal pocket at least 5 consecutive times.

29. The method of claim 28, wherein said solid biodegradable oral delivery device is inserted into the periodontal pocket at least 6 consecutive times.

30. The method of claim 27, wherein said solid biodegradable oral delivery device is inserted into the periodontal pocket at least every week.

31. A method for treating a periodontal disease affecting a periodontal pocket of a patient in need comprising inserting a solid biodegradable oral delivery device into the periodontal pocket at a frequency of every 7-14 days for at least 4 consecutive times, wherein the solid biodegradable oral delivery device is a controlled release solid unit dosage form suitable for insertion into a periodontal pocket of a patient, comprising a therapeutically effective amount of an active ingredient selected from the group consisting of:
   i) at least one anti-inflammatory agent,
   ii) at least one antibacterial agent, and
   iii) the combination of at least one anti-inflammatory agent and at least one antibacterial agent.

32. The method of claim 31, wherein said solid biodegradable oral delivery device is inserted into the periodontal pocket at least 5 consecutive times.

33. The method of claim 32, wherein said solid biodegradable oral delivery device is inserted into the periodontal pocket at least 6 consecutive times.

34. The method of claim 31, wherein said solid biodegradable oral delivery device is inserted into the periodontal pocket at least every week.

* * * * *